United States Patent
Schlegel

(10) Patent No.: US 9,192,537 B2
(45) Date of Patent: Nov. 24, 2015

(54) MODULAR PLUG CONNECTORS

(75) Inventor: Bernard Schlegel, Rahden (DE)

(73) Assignee: HARTING ELECTRIC GMBH & CO. KG, Espelkamp (DE)

(*) Notice: Subject to any disclaimer, the term of this patent is extended or adjusted under 35 U.S.C. 154(b) by 22 days.

(21) Appl. No.: 14/002,775

(22) PCT Filed: Jan. 23, 2012

(86) PCT No.: PCT/DE2012/100016
§ 371 (c)(1),
(2), (4) Date: Sep. 3, 2013

(87) PCT Pub. No.: WO2012/116692
PCT Pub. Date: Sep. 7, 2012

(65) Prior Publication Data
US 2013/0337680 A1 Dec. 19, 2013

(30) Foreign Application Priority Data

Mar. 3, 2011 (DE) .................. 10 2011 001 064

(51) Int. Cl.
*A61B 19/00* (2006.01)
*H01R 13/60* (2006.01)
*A61G 13/12* (2006.01)
*A61B 6/04* (2006.01)

(52) U.S. Cl.
CPC .......... *A61G 13/1295* (2013.01); *A61B 19/203* (2013.01); *A61G 13/121* (2013.01); *A61G 13/123* (2013.01); *A61G 13/127* (2013.01); *A61G 13/1235* (2013.01); *A61G 13/1245* (2013.01); *H01R 13/60* (2013.01); *A61B 6/0421* (2013.01)

(58) Field of Classification Search
CPC .............. H01R 9/22; H01R 9/24; H01R 9/26; H01R 9/2408; H01R 9/2608; H01R 9/64; H01R 9/2691; H01R 101/00; H01R 13/518
USPC ........ 439/532, 111, 121, 12, 716, 2, 927, 717
See application file for complete search history.

(56) References Cited

U.S. PATENT DOCUMENTS

| 3,824,553 A | 7/1974 | Glover et al. |
| 5,735,700 A * | 4/1998 | Hohorst .......................... 439/98 |
| 6,146,213 A * | 11/2000 | Yoon .............................. 439/716 |
| 2008/0318476 A1* | 12/2008 | Weber et al. .................. 439/610 |
| 2009/0290845 A1 | 11/2009 | Hoffmann |

FOREIGN PATENT DOCUMENTS

| CH | 697606 | 12/2008 |
| DE | 8010524 | 12/1982 |
| DE | 36 27 899 | 2/1988 |

(Continued)

*Primary Examiner* — Amy Cohen Johnson
*Assistant Examiner* — Oscar C Jimenez
(74) *Attorney, Agent, or Firm* — Jacobson Holman, PLLC

(57) ABSTRACT

A plug connector has a housing body, and a retaining cage is locked in place inside the housing body. At one end the retaining cage encloses a contacting element for electrically contacting a conductor of a cable to be attached, and at the other end the retaining cage encloses the cable sheath of the cable to be attached. Coupling elements for reversible connection of a further plug connector having an identical housing body are provided externally on the housing body on both sides thereof. Fixing elements for fixing the plug connector onto a mounting rail are provided externally on the housing body.

6 Claims, 4 Drawing Sheets

(56) References Cited

FOREIGN PATENT DOCUMENTS

| | | |
|---|---|---|
| DE | 297 01 158 | 3/1997 |
| DE | 202008006934 | 7/2008 |
| GB | 1 536 082 | 12/1978 |

* cited by examiner

MODULAR PLUG CONNECTORS

CROSS-REFERENCE TO RELATED APPLICATIONS

This is a national stage of PCT/DE12/100016 filed Jan. 23, 2012 and published in German, which has a priority of German no. 10 2011 001 064.5 filed Mar. 3, 2011, hereby incorporated by reference.

BACKGROUND OF THE INVENTION

1. Field of Invention

The invention concerns a plug connector which can be fixed on a mounting rail.

This kind of plug connector is required to establish contact between the individual conductors of a connected cable and the contacts of the mating plug or a socket of a device. The individually connected conductors of the connected cable can be metallic conductors, but also glass fiber or similar material.

2. Description of the Prior Art

DE 36 27 899 C1 and DE 80 10 524 U1 both show plug connecting systems in which the individual plug connector housings have means with which they can be connected to one another. Further, they have fixatives with which they can be mounted, singly or in a group, onto mounting rails.

DE 20 2008 006 934 U1 shows a plug connector for optical fibers. The housing bodies each have only one contacting element and can be strung in a row, in which pins molded onto the housing bodies are inserted into suitable recesses of a neighboring housing body.

If the number of plug connectors strung in a row exceeds a certain number, the plug connector row becomes unstable, at which point, for instance, a mounting rail as a base would be meaningful (top hat rail). The housing bodies of DE 20 2008 006 934 U1 have, however, no such suitable fixative for mounting onto such a mounting rail. Therefore, such plug connectors cannot, for example, be installed in a switching cabinet.

SUMMARY OF THE INVENTION

The object of the invention lies in suggesting a plug connector which is versatile and easy to manufacture.

The object is attained by the modular connector described herein.

Advantageous features of the invention are also described herein.

The plug connector according to this invention is surrounded by a housing body.

The housing body is advantageously developed as one piece. This can be done through known plastic injection molding techniques—in the case of a plastic housing—or through known zinc pressure die casting processes—in the case of a metallic housing.

It is also possible to fashion the housing body out of a composite material, for example out of a combination of metal and plastic.

A holding cage is snapped in securely within the housing body.

The holding cage is essentially fashioned as a hollow cylinder. On one end, the holding cage has two arms pointing in the axial direction, which grasp securely around a contact element. At the other end, the holding cage grasps the cable sheath of a cable that is to be connected to the plug connector. One conductor of the cable is connected to the contact element by means of a crimp connector.

Coupling elements have been provided on both sides of the outside of the housing body which enable it to couple two or more plug connectors with similar housing bodies with one another.

Preferably, one coupling element is shaped like an arch-shaped groove and the other coupling element like a cylindrical pin. The cylindrical pin of one housing body is meant to be introduced into the arch-shaped groove of the similar housing body that is to be coupled. Thus, several plug connectors with similar housing bodies can be strung in a row.

When stringing them in a row, only the housing bodies have to be similar. The internals of the plug connectors can be quite different. Thus, for instance, multi-poled electrical plug connectors can be combined with single-poled optical-fiber plug connectors. As a result, a high modularity of a plug connector arrangement can be achieved. A plug connector arrangement is also known as a system of plug connectors.

Additionally, fixatives have been provided on the outside of the housing bodies, which enable the plug connectors to be fixed to a mounting rail, for example a top hat rail.

The plug connectors can be coupled to each other by means of the coupling elements and can additionally be fixed securely onto a mounting rail.

The fixatives consist of a combination of fixing lugs and spring pins. The fixing lugs are arranged axially and attach to a collar on the mounting rail. The fixing lugs are flexible and can deflect initially when snapping onto the mounting rail, before they snap on behind another collar of the mounting rail.

The plug connector is completed by a cable gland that provides strain relief to the cable and serves to seal the housing body against media like dust and water.

If a desired number of plug connectors are in a row on a mounting rail, this is also known as a system of plug connectors.

To connect two systems of plug connectors with one another, the mounting rails on which the systems are fixed must be joined together. This is implemented by means of a locking device which connects the individual mounting rails securely with one another, so that the plug connectors opposite these can also be connected with one another.

The locking device consists of a passive locking part and an active locking part. The active locking part has the locking elements with which the passive locking part is attached to the active locking part.

When locking the active with the passive locking part, the mounting rails of the systems of plug connectors are brought together and joined with one another. Further, the individual plug connectors lying opposite each other are contacted with each other.

Advantageously, the locking elements of the passive locking part form a knee action lock. Thereby, a particularly stable lock is achieved.

To facilitate the joining of the two mounting rails, the locking device has a guide way. The guide way consists of a bolt on the active locking part which is guided into an opening intended for this purpose in the passive locking part during the locking process. The passive locking part has fixatives on both sides, with which a mounting rail can be fixed. Thus, two mounting rails can be arranged, statically stable, over one another—that is, horizontally separated from each another.

Due to the coupling with each other of the passive and the active locking part, connected systems of plug connectors can be arranged separated horizontally and in a statically stable manner. By means of the locking device, many systems of plug connectors can be arranged over one another to build what are known as plug connector arrays.

BRIEF DESCRIPTION OF THE DRAWINGS

An example of an execution of the invention is shown in the drawings and will be elaborated below. Shown are.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
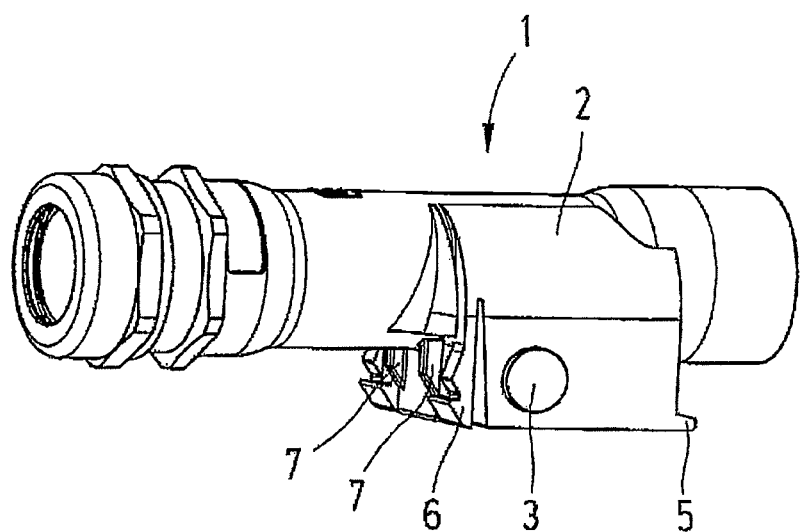
FIG. 1 a perspective presentation of a plug connector.
Figure 2:
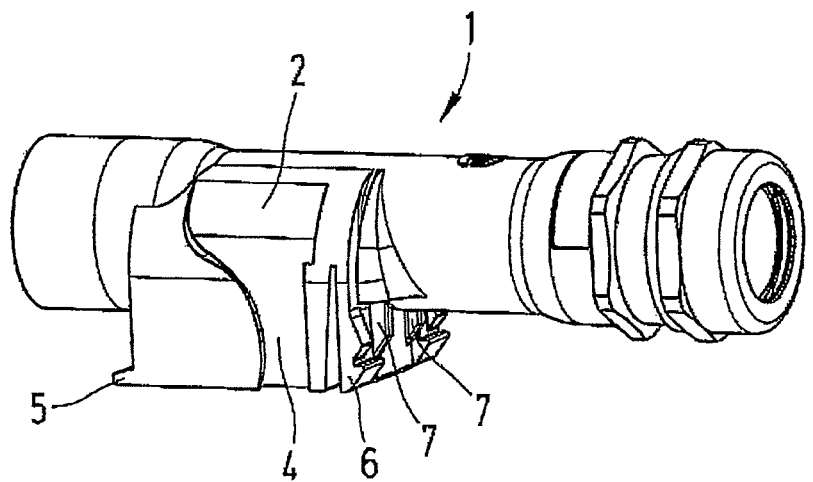
FIG. 2 another perspective presentation of the plug connector.

FIGS. 1 and 2 show perspective representations of an example of an execution of the plug connector as per the invention. The invention is, however, not restricted to the example of execution shown here.

Figure 3:
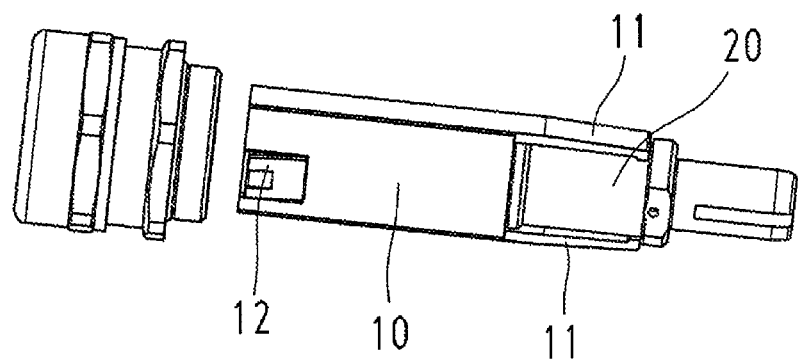
FIG. 3 a perspective presentation of the plug connector without base body.

The plug connector 1 is surrounded by a base body 2. Inside the hollow base body 2 there is a holding cage 10 snapped in securely. FIG. 3 shows the plug connector 1 without base body 2. The holding cage 10 has snap-in elements 12 at one end, which mesh with matching undercuts (not shown) within the base body and thus fix the holding cage 10 in the base body 2. The cable sheath of the connecting cable (not shown) also penetrates into the holding cage at this end.

At the other end, the holding cage has arms 11, which grip around the contacting element 20. Due to this, the contacting element 20 is fixed along the axial symmetry axis in the base body 2.

As already mentioned above, the opposite end of the holding cage 10 is penetrated by the cable sheath of the connecting cable. The conductor of the connecting cable is crimped onto the contacting element.

Figure 4:
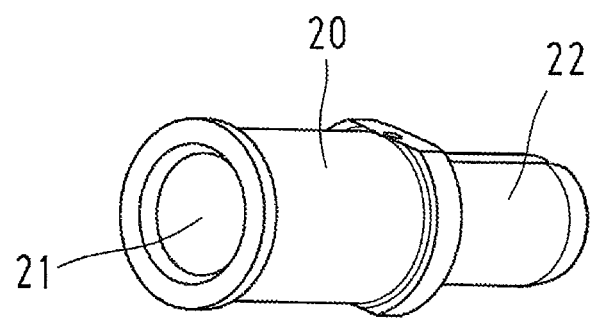
FIG. 4 a perspective presentation of a contacting element.
Figure 5:
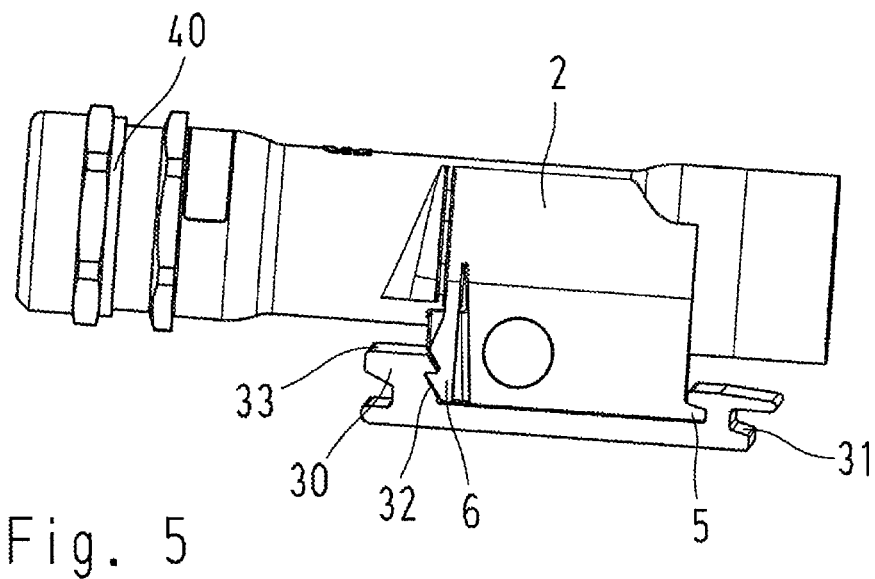
FIG. 5 a side view of a plug connector mounted on a mounting rail.

FIG. 4 shows a perspective representation of the contacting element 20. On one side, the contacting element 20 has a crimp opening 21 for taking up the conductor of the cable that is to be connected. The other side of the contacting element 20 is fashioned in this version as a contact pin 22. It can, however, also be fashioned as a socket contact.

The invention is not restricted to single contact plug connectors. The contacting element 20 can also have several crimp openings 21 and contacts 22 for the purpose of connecting multi-core cables.

The base body 2 surrounds a cylindrical pin 3 on one side and on the opposite side, an arch-shaped groove 4. The pin 3 of a plug connector 1 is capable of being inserted in the groove 4 of another plug connector 1. Thus, several plug connectors 1 can be strung out in a row or coupled with one another. When a desired number of plug connectors is arrived at, one refers to this as a system of plug connectors 1, 1'.

Fixing lugs 5 and spring pins 6 are additionally provided on the base body 2, which together facilitate the reversible fixing of the plug connector 1 on a mounting rail 30. The fixing lugs 5 grip in the undercut 31 of the mounting rail 30. While flipping down the plug connector 1 in the direction of the mounting rail 30, the spring pins are first bent back by a beveled ring 33, in order to then grip onto another undercut 32 of the mounting rail 30.

The base body 2 further surrounds supporting contours 7, which prevent the force, resulting from a movement of the plug connector 1 on the mounting rail 30 in the plugging direction, from being fully imposed on the spring pins.

The plug connector 1 is equipped with a cable gland 40 which is generally known state of the art. Therefore the cable gland will not be discussed in further detail here. The cable gland 40 is meant to act as a pull relief for the connecting cable and for sealing the base body 2 against media such as dust and water.

Figure 6:
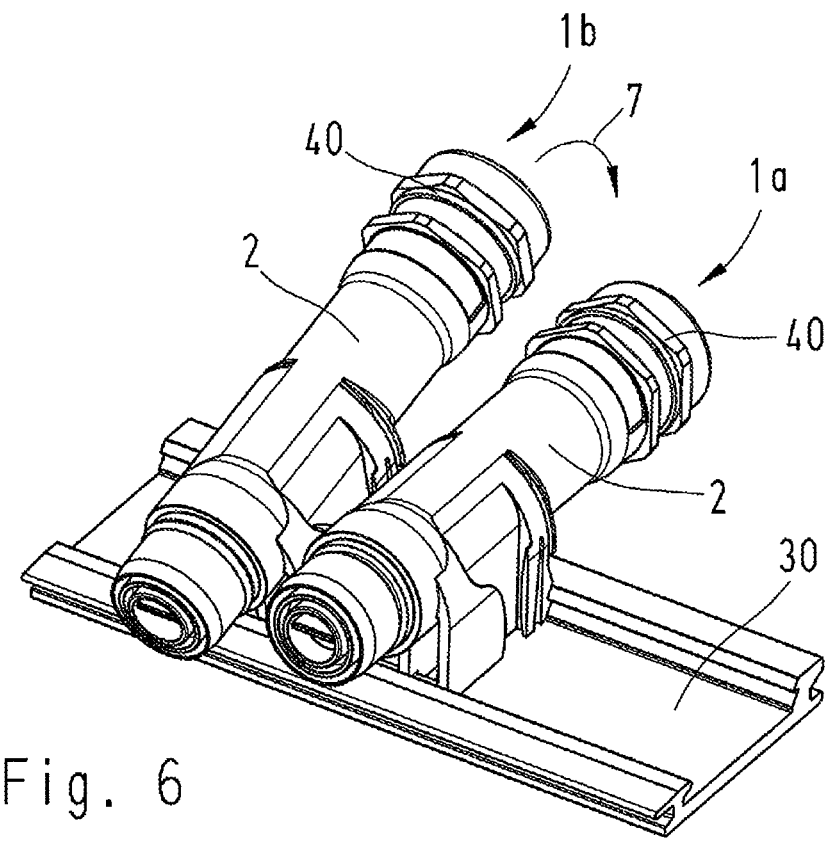
FIG. 6 a perspective presentation of two plug connectors during a coupling process, FIG. 7 a perspective view of two plug connector systems connected to each other and FIG. 8 a side view of the locking device.

FIG. 6 shows the coupling procedure of two plug connectors on the mounting rail 30. One plug connector 1a is already fixed on the mounting rail. The fixing lugs 5 of the plug connector 1b that is to be connected to it are first placed in the undercut 31. The plug connector 1b can then be moved in the direction of the arrow 7 towards the mounting rail 30. The arch-shaped groove of the plug connector 1b grips behind the cylindrical pin 3 of the plug connector 1a. Because of the arched shape of the groove 4, the plug connector 1b can be moved in the direction of the arrow 7. Finally, as described above, the spring pins snap into the undercut 32 of the mounting rail 30. The plug connectors 1a and 1b are coupled with one another as well as fixed on the mounting rail 30.

Exactly the reverse procedure is followed when uncoupling a plug connector from a modular system of plug connectors. The spring pins 6 must first be manually pressed out of the undercut 32. The plug connector can subsequently be disengaged against the direction of arrow 7 from the neighboring plug connector and the mounting rail 30.

Figure 8:
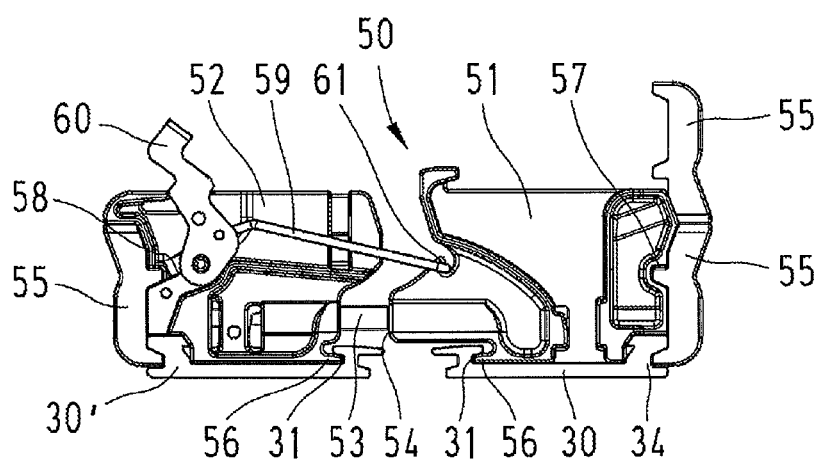

FIG. 8 shows the side view of a locking device 50. The locking device 50 consists of a passive locking part 51 and an active locking part 52.

The active 52 as well as the passive locking part 51 have lugs 56 that can be introduced into undercuts 31 of the mounting rail 30. Both locking parts 51, 52, can be fixed onto the relevant mounting rail 30, 30' with the help of a connector 55. The connector 55 grips simultaneously into a notch 57, 58 of the locking part 51, 52 and into the rear groove 34 of the mounting rail 30.

A guide way is provided for easy joining of locking parts 51, 52. The passive locking part 51 surrounds an opening 54, in which a bolt 53 of the active locking part 52 can be inserted.

The locking of both locking parts 51, 52 is achieved through a tensioning spring 59 attached to the locking part 52, which is connected to a tensioning lever 60 (also attached to the active locking part 52). The tensioning spring 59 is placed over a tensioning lug 61 of the passive locking part 51. By actuating the tensioning lever 60, both the locking parts 51, 52 are brought together and reversibly joined to each other. The combination of tensioning lug 61, tensioning spring 59 and tensioning lever 60 works on the principle of knee lever action and thereby simultaneously ensures a particularly stable coupling of the locking parts 51, 52 and the plug connectors 1, 1' in contact with each other. Furthermore, the knee lever action supports the unlocking procedure.

Figure 7:
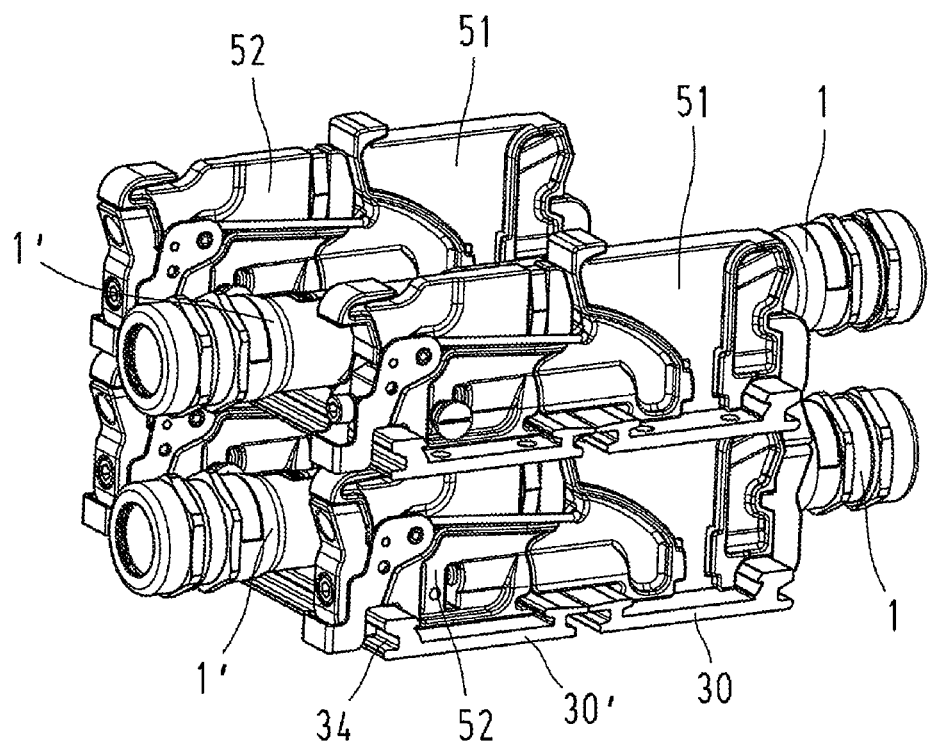

FIG. 7 shows several levels of systems of plug connectors 1, 1'. Two systems of plug contactors 1, 1' lying opposite each other are in contact with each other over the locking device 50. A mounting rail 30, 30' can be fixed on both sides of the locking device 50. Thus, several systems of plug connectors 1, 1' can be arranged equally spaced from each other.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

LIST OF REFERENCE NUMBERS

Modular Plug Connectors

| | |
|---|---|
| 1 | Plug connector |
| 2 | Base body |
| 3 | Cylindrical pin |
| 4 | Arch-shaped groove |
| 5 | Fixing lugs |
| 6 | Spring pins |
| 7 | Supporting contour |
| 10 | Holding cage |
| 11 | Arm |
| 12 | Snap-in element |
| 13 | |
| 14 | |
| 20 | Contacting element |
| 21 | Crimp opening |
| 30 | Mounting rail |
| 31 | Undercut |
| 32 | Undercut |
| 33 | Ring |
| 34 | Groove |
| 40 | Cable gland |
| 50 | Locking device |
| 51 | Passive locking part |
| 52 | Active locking part |
| 53 | Bolt |
| 54 | Opening |
| 55 | Connector |
| 56 | Lug |
| 57 | Notch |
| 58 | Notch |
| 59 | Tensioning spring |
| 60 | Tensioning lever |
| 61 | Tensioning lug |
| 62 | |

What is claimed is:

1. A plug connector that can be fixed on a mounting rail, said plug connector comprising:
   a housing body;
   fixatives for fixing the plug connector onto the mounting rail, the fixatives being provided on an outside of the housing body;
   a contacting element for electrical contact of a conductor of a cable that is to be connected at one end thereof, and a cable sheath of the cable at another end thereof;
   a holding cage that is snappable onto an inside of the housing body,
   the holding cage gripping around the contacting element; and
   on both sides of the outside of the housing body, coupling elements provided for the reversible connection with another plug connector with a similar housing body,
   one of the coupling elements being an arch-shaped groove and the other coupling element being a cylindrical pin, with the arch-shaped groove being configured to slidably engage the cylindrical pin and effect the reversible connection as the plug connector is rotated vertically toward the mounting rail.

2. The plug connector according to claim 1, wherein the housing body includes a cable gland for cable pull relief and sealing.

3. The plug connector according to claim 1, wherein the housing body is configured as one piece.

4. The plug connector according to claim 1, wherein the fixatives comprise a combination of fixing lugs and spring pins.

5. A plug connector that is reversibly fixable to a mounting rail, said plug connector comprising:
   a housing body;
   a first fixing element and a second fixing element for reversibly fixing the plug connector to the mounting rail, the first fixing element and the second fixing element being provided on an outside of the housing body;
   a contacting element for electrical contact of a conductor of a cable that is to be connected at one end thereof, and for contact with a cable sheath of the cable at another end thereof;
   a holding cage that is snappably fixable onto an inside of the housing body, the holding cage being configured to grip around the contacting element; and
   on opposed sides of the outside of the housing body, a first coupling element and a second coupling element provided for reversibly connecting the plug connector to another plug connector adjacent thereto, the first coupling element being configured as an arch-shaped groove, and the second coupling element being configured as a cylindrical pin that is slidably and reversibly receivable into the arch-shaped groove of the adjacent plug connector as the plug connector is moved vertically toward the mounting rail as to provide the reversible connection between the plug connector and the adjacent plug connector.

6. The plug connector of claim 5, wherein the plug connector and the connected adjacent plug connector are removable from the mounting rail while connected together.

* * * * *